United States Patent [19]
Oba

[11] Patent Number: 5,038,800
[45] Date of Patent: Aug. 13, 1991

[54] SYSTEM FOR MONITORING PATIENT BY USING LAN

[75] Inventor: Kazuo Oba, Tokyo, Japan

[73] Assignee: Fukuda Denshi Co., Ltd., Tokyo, Japan

[21] Appl. No.: 390,734

[22] Filed: Aug. 8, 1989

[30] Foreign Application Priority Data

Mar. 3, 1989 [JP] Japan .................................... 1-51671

[51] Int. Cl.$^5$ .............................................. A61B 5/04
[52] U.S. Cl. .................................. 128/904; 128/903; 128/696; 364/413.02
[58] Field of Search ...................... 364/413.06, 413.02; 128/903, 904, 696

[56] References Cited

U.S. PATENT DOCUMENTS

| | | | |
|---|---|---|---|
| 3,986,498 | 10/1976 | Lewis .................................... | 128/904 |
| 4,296,756 | 10/1981 | Dunning et al. .................... | 128/904 |
| 4,356,475 | 10/1982 | Neumann et al. .............. | 364/413.02 |
| 4,736,295 | 4/1988 | Lachiver et al. ............... | 364/413.06 |

OTHER PUBLICATIONS

Data Communications, Computer Networks and OSI, by Fred Halsall, published by Addison-Wesley Publishing Co., 1988, p. 6.

*Primary Examiner*—Francis Jaworski
*Assistant Examiner*—George Manuel
*Attorney, Agent, or Firm*—Sughrue, Mion, Zinn, Macpeak & Seas

[57] ABSTRACT

A system for monitoring a patient by using a local area network (LAN) to connect a central monitor, located at a nurse's station, to one or more bedside monitors, wherein the bedside monitor measures the patient's condition, for instance an electrocardiogram (ECG). The LAN provides data from the bedside monitor to the central monitor at a rate sufficient for the central monitor to display all information contained within the bedside monitor in substantially real time. The LAN also allows a user at the central station or at another bedside monitor to remotely read or adjust the bedside monitor settings.

11 Claims, 2 Drawing Sheets

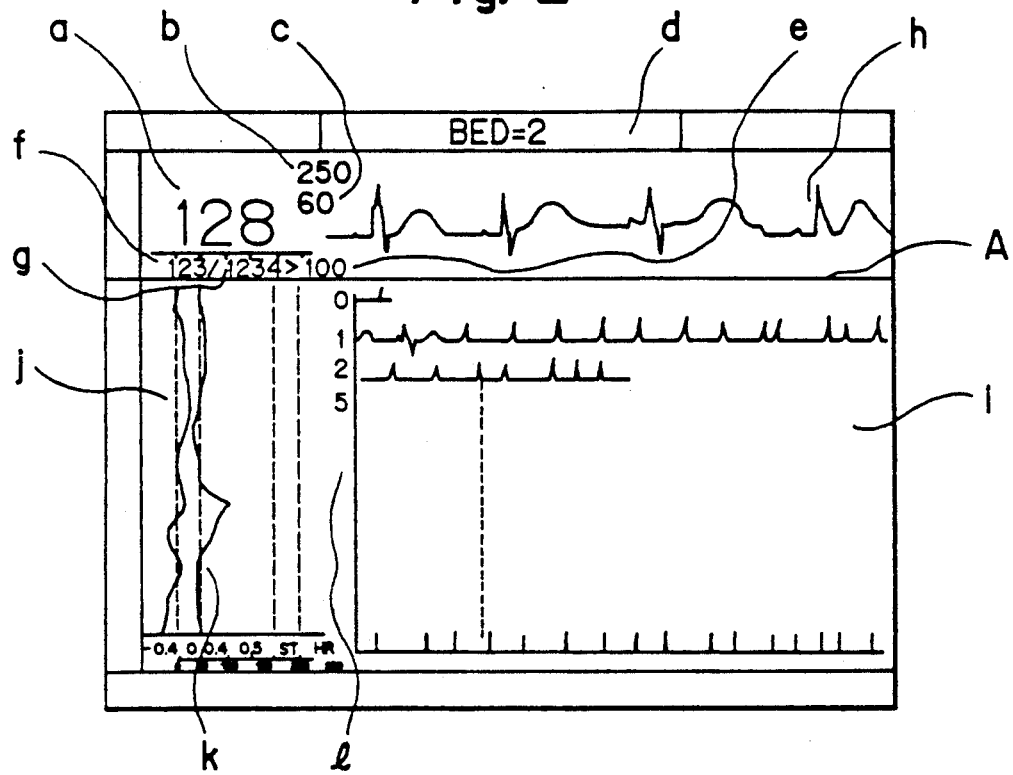
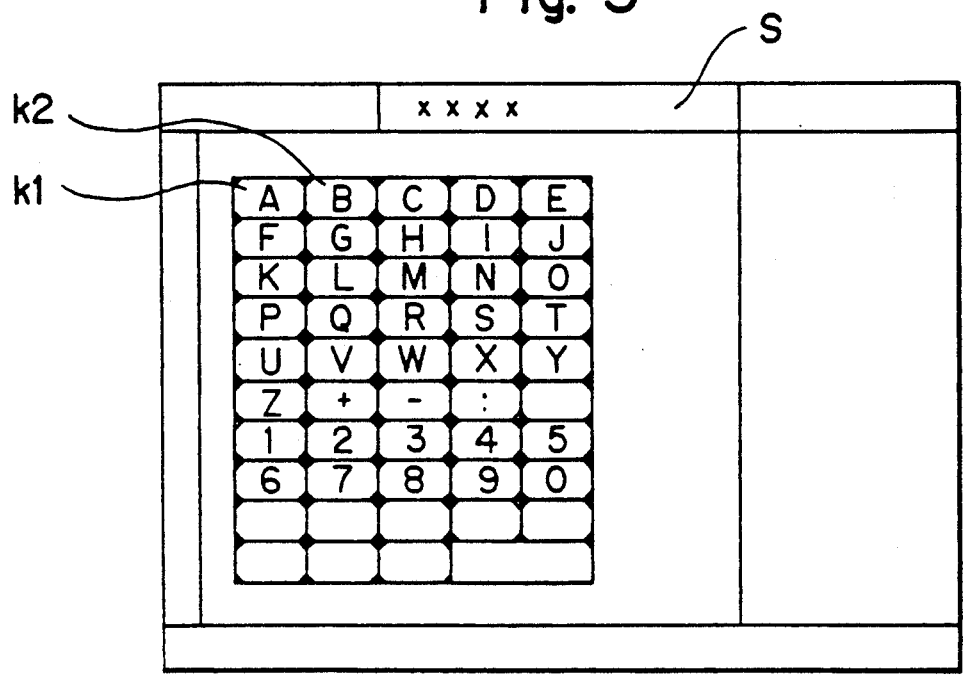

SYSTEM FOR MONITORING PATIENT BY USING LAN

BACKGROUND OF THE INVENTION

1. Field of the Invention

The present invention relates to a system for monitoring a patient by using a LAN. More particularly, it relates to a system for monitoring a patient by using a LAN, in which an apparatus having no data, such as a central monitor, and an apparatus having data, such as a bedside monitor, are connected by the LAN.

2. Description the Related Art

Generally, an apparatus for monitoring, that is to say, a monitor has been originally used in order to continually monitor the electrocardiogram etc. of a patient with an advanced disease accommodated in ICU, CCU etc.

However, the range of the use of the monitor has been recently increasing and, for example, the monitor is also used for patients housed in the general ward.

Accordingly, the monitor has become an apparatus necessary to clinical medicine.

The monitor is divided into a monitor for monitoring a single patient, that is to say, a bedside monitor, and a monitor for monitoring a great many patients from a nurse's station, that is to say, a central monitor.

The bedside monitor receives data from an electrocardiogram or similar device connected to a patient.

However, the central monitor has no data, because the central monitor is located in the nurse's station away from a patient, and the electrocardiogram is not directly connected thereto.

In the conventional system for monitoring a patient, the central monitor having no data and the beside monitor having data are connected by cable.

In this conventional system, the wave form of the living body signal is transmitted in analog, and the other controls or numerical signals are transmitted in digital.

As aforementioned, the central monitor and the bedside monitor are connected by cable.

However, the cable has a very low transmission rate, since the cable transmits both analog and digital signals. Therefore, the overall system processes data late (i.e. there is a delay between the ECG registering a patient and the central monitor displaying the ECG measurement). In addition the system only processes data in one direction.

Hence, in the prior art, all the contents of the bedside monitor cannot be observed at the central monitor and all the setting operations of the bedside monitor cannot be performed at the central monitor.

That is, the prior art system has the defect that the control of observing all the contents and of doing all the setting operations, of the bedside monitor, cannot be respectively carried out by the central monitor.

SUMMARY OF THE INVENTION

An object of the present invention is that all the control of the apparatus having data can be carried out on the side of the apparatus having no data, in the system for monitoring a patient.

The above-mentioned object can be achieved by a system which monitors patients by using a LAN comprising a first apparatus having no data and a second apparatus having data which are mutually connected by the LAN. The first apparatus having no data indicates the complete contents and allows all setting operations of said second apparatus having data.

BRIEF DESCRIPTION OF THE DRAWINGS

Further features and advantages of the present invention will be apparent from the ensuring description with reference to the accompanying drawings, wherein:

FIG. 2 is a detailed drawing of the embodiment of the present invention;

FIG. 3 is a detailed drawing of the embodiment of the present invention.

DETAILED DESCRIPTION OF THE PREFERRED EMBODIMENT

Figure 1A:
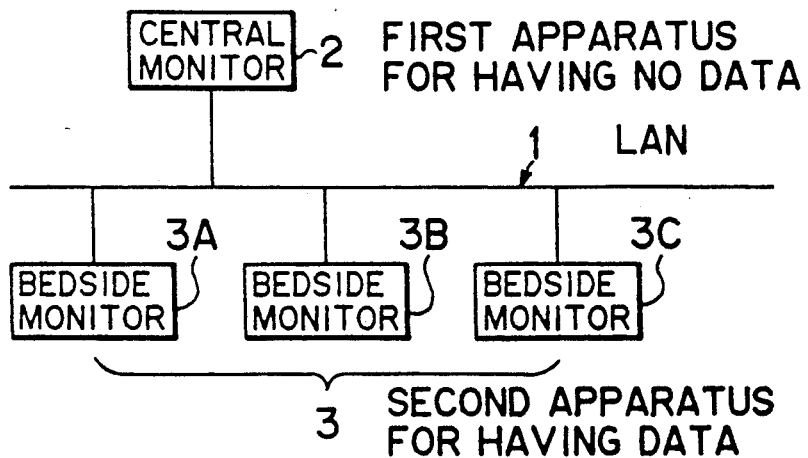
FIG. 1A is a drawing of the first embodiment of the present invention.

FIG. 1A is a drawing of the first embodiment of the present invention, wherein reference numeral 1 shows LAN, 2 a first apparatus having no data, 3 a second apparatus having data.

FIG. 1A is the case where a first apparatus 2 having no data and a second apparatus 3 having data are mutually connected by the LAN. The LAN side with the first apparatus 2 having no data, indicates all of the contents and allows all the settings operations of said second apparatus 3 having data, at substantially real time (i.e. the first apparatus 2 will be able to display any information displayed by the second apparatus 3 at substantially the same time). This fast data transfer provides the nurse with a patients current condition.

There is, for example, a central monitor, as the first apparatus 2 having no data, and there is, for example, a bedside monitor, input box or receiver, as the second apparatus 3 having data.

LAN 1 is short for Local Area Network, which has twice the capacity of cable used in the prior art and which has a signal transmitting speed about one hundred times that of cable used in the prior art.

Moreover, the transmitted signal is a digital signal which carries out bidirectional communication in the LAN 1, and provides the high speed communication IC characteristics of a Local Area Network.

Hence, in the system for monitoring patients with the above constitution (see FIG. 1A), all the contents of the second apparatus 3 having data are able to be observed, by the first apparatus 2 having no data.

As FIG. 1A indicates the second apparatus 3 having data is the same as that in the first apparatus 2 having no data.

FIG. 2 represents an example display output, which may be shown on either the bedside or the central monitor. This display, which resembles the monitor display in Japanese Patent Appliction No. 1-27214 filed Feb. 6, 1989, shows the electrocardiograph output scaled over several time intervals, each of which ends at a current point in time.

The display indicates, via bed indicator d, which patient the current cardiographic output represents. In FIG. 2, the current output represents bed #2.

More specifically, the boundary line A separates upper and lower display portions, which indicate time periods of different lengths.

The lower portion indicates the electrocardiogram output i for longer periods, such as a 3 minute time period, while the upper portion indicates the electrocardiogram output h for a shorter period, such as a 6 second time period.

In FIG. 2, reference numeral a shows an average heart beat, b the upper limit of the heat beat, c the lowest limit of the heart beat, f the arrhythmia number per minute, g the arrhythmia number per hour, e the arrhythmia value smaller than the content of the above f, j the trend of ST, k an instant heart beat, 1 the arrhythmia number per each hour zone of the electrocardiogram output i.

The above described pictures of the basic display indicated in the bedside monitor are also able to be observed on the central monitor.

The basic picture is indicated, when the condition of the patient is normally monitored in this system.

On the other hand, the control of all the settings for the second apparatus 3 having data, is carried out on the first apparatuses' side of the LAN.

For example, the operation of setting (see FIG. 3) the name of the patient in the bedside monitor 3A is able to be carried out on the central monitor's 2 side of the LAN.

FIG. 3 shows the picture wherein the name of the patient is designated.

On the picture, keyboards k1, k2 . . . are indicated and, when each key is pushed, the corresponding name is indicated in the upper portion S.

The indication of all the contents and all the setting operations, as aforementioned, are also capable of being carried out between the second apparatuses having data.

For example, when bedside monitors 3A, 3B and 3C are connected with LAN 1 as shown in FIG. 1A, between any two bedside monitors, the indication of all the contents and setting of all the operations of one bedside monitor, are able to be carried out, by another bedside monitor.

Figure 1B:
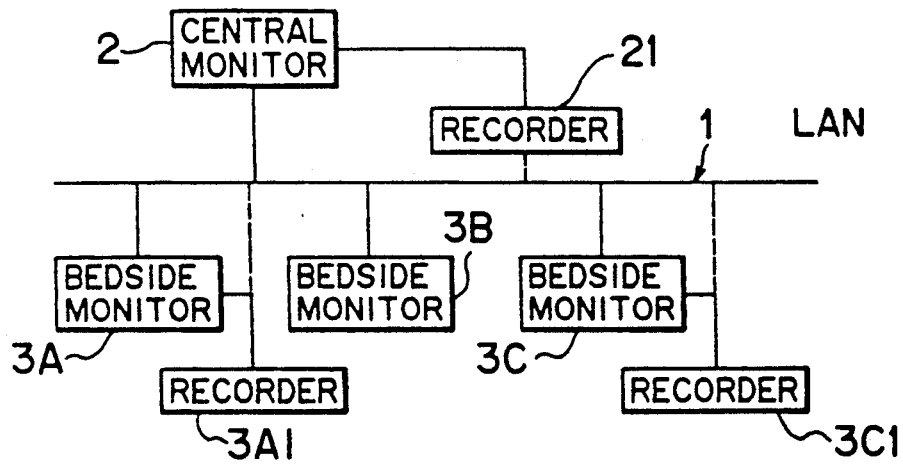
FIG. 1B is a drawing of the second embodiment of the present invention.

FIG. 1B is a drawing of the second embodiment of the invention, which is generally the case where recorders are connected with both of the first apparatus 2 having no data and the second apparatus 3 having data, or with anyone of them, and the recorders perform the same recording functions between monitors. Especially, in FIG. 1b, a recorder 21 is connected with the central monitor, as the first apparatus 2 having no data, and recorders 3A1 and 3C1 are respectively connected with bedside monitors 3A and 3C as the second apparatuses 3 having data. Hence, for example, the recorder 3A1 connected directly with the bedside monitor 3A is able to be used by the bedside monitor 3B, via the LAN as if connected directly with the bedside monitor 3B.

Figure 1C:
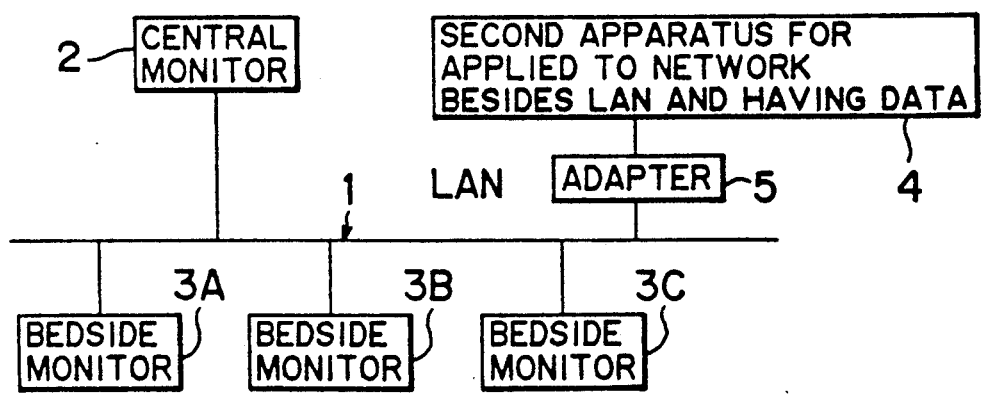
FIG. 1C is a drawing of the third embodiment of the present invention.

In FIG. 1B, the recorders 21, 3A1 and 3C1 perform the same functions, and may be directly connected with LAN 1, as shown by dotted line. FIG. 1C is a drawing of the third embodiment of the invention, which is the case where a second apparatus 4 is applied to the network and is connected with LAN 1 through an adapter 5. Hence, a system for monitoring patients is constituted by the second apparatus 4 (an external monitor) having data, LAN 1, and the first apparatus 2 having no data. This external apparatus 4 may supply data to the system, as does the bedside monitors, or receive data from the system, as does the central monitor. This system has quite the same function as the system for monitoring patients, which is constituted by the second apparatus 3 having data, LAN 1, and the first apparatus 2 having no data. That is to say, the indication of all the contents and the operation of all the settings of the second apparatus 4 for having data, are able to be carried out, on the first apparatus' 2 side having no data.

According to the present invention, in a system for monitoring patient by using LAN, the first apparatus 2 having no data and the second apparatus 3 having data are mutually connected with a LAN, and the indication of all the contents and the operation of all the settings of the second apparatus 3 having data, are able to be carried out, on the side of the first apparatus 2 having no data. The LAN system of the present invention, differs from the conventional cable system, since the present invention transmits all information digitally; namely the control signals, numerical data, and the wave form representing a patient's present condition. The present LAN system offers high speed and mutual direction communication. Therefore, since the present system for monitoring a patient is constituted by connecting the first apparatus 2, having no data, with the second apparatus 2, having data, through LAN 1, the indication of all the contents of the second apparatus 3 having data, are able to be carried out, on the side of the first apparatus 2 having no data. The present invention has the effect that all the control operations for the apparatus having data may be performed on the side of the apparatus having no data.

What is claimed is:

1. A system, including a LAN, for monitoring a patient comprising:
    a bedside monitor for receiving patient data from patient monitoring equipment and transmitting said patient data over said LAN,
    a central monitor for receiving said patient data transmitted over said LAN, and for displaying said patient data, said bedside and central monitors being mutually connected over said LAN, wherein said LAN provides said central monitor with only digital patient data transmitted from said bedside monitor, and said LAN allows said central monitor to control the operation of said bedside monitor through bidirectional digital data transfer.

2. A system, including a LAN, for monitoring a patient according to claim 1, wherein said central monitor includes means for selecting one bedside monitor from a plurality of bedside monitors, after said selection said central monitor displays in substantially real time any patient data display by said selected bedside monitor.

3. A system including a LAN, for monitoring a patient according to claim 1, further comprising a plurality of said bedside monitors connected to said LAN, wherein said LAN includes means for providing each of said plurality of said bedside monitors with patient data from any other of said plurality of bedside monitors and said LAN includes means for allowing each of said plurality of said bedside monitors to control patient settings of any another of said plurality of said bedside monitors.

4. A system, including a LAN, for monitoring a patient according to claim 1, wherein said system includes a plurality of central monitors.

5. A system, including a LAN, for monitoring a patient according to claim 1, wherein said system includes a plurality of bedside monitors.

6. A system, including a LAN, for monitoring a patient according to claim 1, wherein said bedside monitor is an input box.

7. A system, including a LAN, for monitoring a patient according to claim 1, wherein said bedside monitor is a receiver.

8. A system, including a LAN, for monitoring a patient according to claim 1, wherein said central and bedside monitors are connected with recorders respectively.

9. A system, including a LAN, for monitoring a patient according to claim 8, wherein said recorders perform the same recording functions.

10. A system, including a LAN, for monitoring a patient according to claim 8, wherein said recorders are directly connected with the LAN.

11. A system, including a LAN, for monitoring a patient according to claim 1, further comprises:
an external monitor connected to said LAN through an adaptor, said external monitor supplying additional data to and receiving data from said central and bedside monitors.

* * * * *